US012570724B2

(12) United States Patent
Yang et al.

(10) Patent No.: US 12,570,724 B2
(45) Date of Patent: Mar. 10, 2026

(54) PREPARATION METHOD FOR BIOSYNTHESIS OF HUMAN BODY STRUCTURAL MATERIAL

(71) Applicant: SHANXI JINBO BIO-PHARMACEUTICAL CO., LTD., Shanxi (CN)

(72) Inventors: Xia Yang, Shanxi (CN); Xiaobin Lan, Shanxi (CN); Zhenrui He, Shanxi (CN); Lingling Wang, Shanxi (CN); Yongjian Zhang, Shanxi (CN); Xin Liu, Shanxi (CN); Haihong Song, Shanxi (CN)

(73) Assignee: SHANXI JINBO BIO-PHARMACEUTICAL CO., LTD., Taiyuan (CN)

( * ) Notice: Subject to any disclaimer, the term of this patent is extended or adjusted under 35 U.S.C. 154(b) by 0 days.

(21) Appl. No.: 19/005,323

(22) Filed: Dec. 30, 2024

(65) Prior Publication Data

US 2025/0129138 A1 Apr. 24, 2025

Related U.S. Application Data

(63) Continuation of application No. PCT/CN2023/077661, filed on Feb. 22, 2023.

(30) Foreign Application Priority Data

Aug. 23, 2022 (CN) .......................... 202211017546.9

(51) Int. Cl.
| | |
|---|---|
| *C07K 14/78* | (2006.01) |
| *A61K 38/00* | (2006.01) |
| *A61L 27/24* | (2006.01) |
| *C12N 5/00* | (2006.01) |
| *C12N 15/63* | (2006.01) |
| *A61K 8/65* | (2006.01) |
| *A61L 15/32* | (2006.01) |
| *A61L 31/04* | (2006.01) |

(52) U.S. Cl.
CPC ............ *C07K 14/78* (2013.01); *C12N 5/0068* (2013.01); *C12N 15/63* (2013.01); *A61K 8/65* (2013.01); *A61K 38/00* (2013.01); *A61L 15/325* (2013.01); *A61L 27/24* (2013.01); *A61L 31/044* (2013.01); *C12N 2533/54* (2013.01); *C12N 2533/90* (2013.01)

(58) Field of Classification Search
CPC .. C07K 14/78; C12N 5/0068; C12N 2533/54; C12N 2533/90; A61K 38/00; A61K 8/65; A61L 15/32; A61L 27/24; A61L 15/325; A61L 31/044
See application file for complete search history.

(56) References Cited

U.S. PATENT DOCUMENTS

| | | | | |
|---|---|---|---|---|
| 9,676,837 B2 * | 6/2017 | Viswanathan | ......... | C07K 14/78 |
| 10,227,394 B2 * | 3/2019 | Chen | ..................... | A61K 47/42 |

FOREIGN PATENT DOCUMENTS

| | | | |
|---|---|---|---|
| CN | 108165593 A | 6/2018 | |
| CN | 109072255 A | 12/2018 | |
| CN | 113185604 A | 7/2021 | |
| CN | 113621053 A | 11/2021 | |
| WO | WO-2017161180 A1 * | 9/2017 | ........... C12N 5/0625 |

OTHER PUBLICATIONS

"Collagen alpha-1(VII) chain precursor [*Homo sapiens*]", NCBI Reference Sequence: NP_000085.1, accessed from https://www.ncbi.nlm.nih.gov/protein/NP_000085.1. 7 pages total. (Year: 2025).*

* cited by examiner

*Primary Examiner* — Terry A Mckelvey
*Assistant Examiner* — Andrew T Moehlman
(74) *Attorney, Agent, or Firm* — Lando & Anastasi, LLP

(57) ABSTRACT

The present application provides a preparation method for biosynthesis of a human body structural material. A polypeptide has the amino acid sequence of SEQ ID NO. 4, 5 or 6. Recombinant type-VII humanized collagen prepared in the present application has high activity of promoting cell proliferation and does not produce an immune response when applied to a human body, and the preparation method therefor is novel and can obtain the recombinant type-VII humanized collagen on a large scale, and is widely applied in the preparation of human body structural materials.

8 Claims, 5 Drawing Sheets

Specification includes a Sequence Listing.

PREPARATION METHOD FOR BIOSYNTHESIS OF HUMAN BODY STRUCTURAL MATERIAL

CROSS-REFERENCE TO RELATED APPLICATIONS

This application is a continuation of International Patent Application No. PCT/CN2023/077661 filed on Feb. 22, 2023 which claims the priority benefit of the Chinese Patent Application No. 202211017546.9 titled "PREPARATION METHOD FOR BIOSYNTHESIS OF HUMAN BODY STRUCTURAL MATERIAL", filed on Aug. 23, 2022. The content of the aforementioned application is incorporated herein by reference.

SEQUENCE LISTING

A sequence listing contained in the file named "C23W378801US" which is 36,182 bytes and created on Dec. 17, 2024, is filed electronically herewith and incorporated by reference in its entirety.

TECHNICAL FIELD

The present application belongs to the field of synthetic biotechnology and relates to a preparation method for the biosynthesis of human body structural material.

BACKGROUND

The structural materials of the human body are mainly structural proteins including collagen. Such proteins have adhesion and support functions for cells and tissues and are the main component of the extracellular matrix.

Collagen is a type of protein widely distributed in human connective tissues and is also the most abundant protein in the human body, accounting for 25% to 35% of the total protein. It is currently found that there are at least 28 collagen subtypes in the human body, which are located in different tissues or organs. Among them, type VII collagen is of a fibrous collagen distributed in the basement membrane area of stratified squamous epithelium, such as skin, oral mucosa, and cervix. Thus, type VII collagen is also called basement membrane collagen. Type VII collagen is the main component of anchoring fibrils in the skin. These fibrils extend from the lamellar dendrites of the epidermal basement membrane to the dermal connective tissue, which contributes to the adhesion between the epidermis and the dermis. Animal experiments have shown that type VII collagen promotes the migration of fibroblasts and the secretion of cytokines, and participates in skin damage and repair through tissue laminin; type VII collagen also corrects malnutrition epidermolysis bullosa by artificial injection of recombinant type VII collagen.

Currently, the crude product of type VII collagen is mainly obtained by extraction from animal tissues or by lentiviral transfection. Unfortunately, type VII collagen has a relatively low content in an organism, and the extraction process of type VII collagen is relatively complicated. Also, animal-derived immune responses are an important reason for the limitation of collagen in application. In contrast, although lentiviral transfection is lower immunogenic, it is difficult to operate and is more limited in the capacity of target genes. With the increasing growth of the collagen industry in our country, the utilization of biosynthetic pathways to obtain collagen has become increasingly mature, especially in humanized collagen, which has been at the forefront of the world. In 2021, the National Medical Products Administration conducted the naming and classification of biosynthetic collagen. Among them, recombinant humanized collagen refers to the full-length or partial amino acid sequence fragment encoded by the gene of the specific type of human collagen prepared by DNA recombinant technology, or a combination containing function fragments of human collagen.

Type VII collagen is a homotrimer composed of three identical al chains, and the molecular form is $\alpha 1 \alpha 1 \alpha 1$ (VII). The three $\alpha 1$ (VII) chains twist together to form a triple chains rope-like molecule of procollagen. Procollagen molecules are secreted by cells and the excess protein fragments are removed from the ends by enzyme treatment. After processing, the procollagen molecules are arranged into long and thin bundles, to form a mature type VII collagen. Each $\alpha 1$ polypeptide chain contains a central collagenous triple helical region, flanked by non-collagenous amino and carboxyl ends. The collagenous structural region is a triple helical domain composed of a characteristic Gly-X-Y repeating sequence. The genetic mutation of type VII collagen causes synthesis disorders or structural abnormalities of collagen, leading to varying degrees of blisters. The symptoms involve the skin, oral mucosa, esophagus, and other sites. Although most are nonsense mutations, missense mutations may still occur, which results in the retention and misfolding of collagen in cells, affecting the connection between the vaginal mucosa and the basement membrane lamina propria.

Currently, type VII collagen has been mainly obtained by enzyme digestion and lentiviral transfection. Enzyme digestion refers to the extraction of type VII collagen derivatives by treating animal-derived tissues with proteases. However, the collagen extracted by this method has lost its original biological activity, and cannot exert the true function of the collagen. Lentiviral transfection refers to the construction of a retroviral vector, followed by cell transfection, and finally purification of type VII collagen. However, the preparation process of this method has defects in that the preparation is difficult and it is not easy to obtain high-purity viruses; the integration of lentiviral vectors in the host genome is random, which may interfere with the expression of genes at the insertion site and neighboring genes; it is difficult to achieve precise control of the number of integrated copies; and the capacity of the target gene is small. Therefore, there is an urgent need for a biosynthetic method for recombinant type VII humanized collagen which overcomes these defects, allowing the wide application as a structural material of the human body.

SUMMARY OF THE INVENTION

In view of the defects of the prior art, the present application designs a core functional region screening and synthesis process of the recombinant humanized type VII collagen. The present application designs a functional region screening and protein synthesis process of recombinant humanized type VII collagen, which is the discovery for the first time.

In one aspect, the present application provides a polypeptide comprising a structure of (repeating unit)$_n$, wherein the repeating unit comprises the amino acid sequence of SEQ ID NO. 1, each repeating unit is directly linked and the number n of the repeating unit is 4-20. In one embodiment, the polypeptide is a recombinant humanized type VII collagen.

In one embodiment, the polypeptide comprises the amino acid sequence of SEQ ID NO. 4.

In one aspect, the present application provides a nucleic acid comprising nucleotide sequence of the polypeptide sequence as described herein. In one embodiment, the nucleic acid further comprises a nucleotide sequence encoding a purification tag. The purification tag may be an His tag, a GST tag, an MBP tag, a SUMO tag, or a NusA tag. In one embodiment, the nucleic acid further comprises a nucleotide sequence encoding a leader sequence.

In one embodiment, the nucleic acid comprises a nucleotide sequence of SEQ ID NO.7.

In one aspect, the present application provides a vector comprising the nucleic acid as described herein. In one embodiment, the nucleic acid may comprise an expression control element operably linked to the nucleic acid. In one embodiment, the expression control element may be a promoter, a terminator, and/or an enhancer.

In one aspect, the present application provides a host cell comprising the nucleic acid as described herein or the vector as described herein. In one embodiment, the host cell is a eukaryotic cell or a prokaryotic cell. In one embodiment, the eukaryotic cell is a yeast cell, an animal cell, and/or an insect cell. In one embodiment, the prokaryotic cell is an *Escherichia coli* cell. In one embodiment, the *E. coli* is *E. coli* BL21.

In one aspect, the present application provides a method for producing the polypeptide as described herein, comprising:

(1) cultivating the host cell as described herein under an appropriate culture condition;

(2) harvesting the host cells and/or culture medium comprising the polypeptide; and (3) purifying the polypeptide.

The purifying step may be performed by the steps selected from the group consisting of (1) crudely purifying the polypeptide in a Ni affinity chromatographic column; (2) adding TEV enzyme for enzyme digestion; (3) finely purifying the polypeptide on an ion exchange column.

In one aspect, the present application provides compositions comprising the polypeptide as described herein, the nucleic acid as described herein, the vector as described herein and/or the host cell as described herein. For example, the composition may comprise a polypeptide. The polypeptide may be at a concentration of more than 1 mg/ml, more than 5 mg/ml, more than 10 mg/ml, or more than 12 mg/ml. In one embodiment, the composition is one or more of biological dressings, human body biomimetic materials, materials for plastic surgery and aesthetics, organoid culture materials, cardiovascular stent materials, coating materials, tissue injection and filling materials, ophthalmic materials, gynaecology and obstetrics biological materials, nerve repair and regeneration materials, liver tissue materials and vascular repair and regeneration materials, 3D printing artificial organ biomaterials, cosmetic raw materials, medicinal auxiliary materials and food additives.

In one aspect, the present application provides use of the polypeptide as described herein, the nucleic acid as described herein, the vector as described herein, and/or the host cell as described herein and/or the composition as described herein in promoting cell adhesion in vitro or in the manufacture of a product or kit for promoting cell adhesion.

In one aspect, the present application provides use of the polypeptide as described herein, the nucleic acid as described herein, the vector as described herein, and/or the host cell as described herein and/or the composition as described herein in the manufacture of high-end medical devices, such as biological dressings, human body biomimetic materials, materials for plastic surgery and aesthetics, organoid culture, cardiovascular stent, coating, tissue injection and filling materials, ophthalmic materials, gynaecology and obstetrics biological materials, nerve repair and regeneration, liver tissue and vascular repair and regeneration, 3D printing artificial organ biological materials, etc.; high-end cosmetic raw materials and medicinal auxiliary materials; and food additives.

In one aspect, the present application provides a method for promoting cell proliferation, comprising contacting the cell with the polypeptide as described herein. Preferably, the cell is an animal cell, such as a mammalian cell.

The embodiments of the present application include:

1. In view of the current research status, the present application provides a method for biosynthesizing recombinant type VII humanized collagen, that is, a method for preparing structural materials of the human body. The specific processes comprise (1) functional region screening and strain construction; (2) large-scale biological fermentation culture and inducible expression of the protein; and (3) purification and optional enzyme digestion of the humanized type VII collagen.

2. According to item 1, functional region screening and strain construction may be conducted as follows: (1) screening functional regions on a large scale to obtain the segment of the target gene; (2) inserting the obtained segment of the target gene into a PET-28a-Trx-His expression vector to obtain a recombinant expression plasmid; and (3) transforming the recombinant expression plasmid into *E. coli* competent cells BL21 (DE3) to obtain positive *E. coli* genetically engineered bacteria by screening.

3. According to item 1, large-scale biological fermentation may be conducted as follows: adding the positive *E. coli* genetically engineered bacteria obtained by screening to a shake flask containing an antibiotic stock solution, and culturing the bacteria in a constant temperature shaker at 220 rpm and 37° C.

4. According to item 1, the inducible expression of the protein may be conducted as follows: (1) cooling the shake flask after the culture to 16-30° C.; (2) adding IPTG stock solution for inducible expression; and (3) placing the bacterial liquid after inducible expression into a centrifuge bottle, and collecting the bacterial cells after centrifugation at 6000 rpm and 4° C. for 12 min.

5. According to item 1, the purification and optional enzyme digestion of the humanized type VII collagen may be conducted as follows: (1) crudely purifying the humanized type VII collagen on a Ni affinity chromatography column; (2) adding TEV enzyme at a certain ratio for enzyme digestion; and (3) finely purifying the humanized type V collagen on an ion exchange column.

6. According to item 2, the screened functional regions are as follows.

(1) The amino acid sequence of recombinant type VII humanized collagen C7P7:

(SEQ ID NO: 4)

GFPGVPGGTGPKGDRGETGSKGEQGLPGERGLRGEPGFPGVPGGTGPKGD

RGETGSKGEQGLPGERGLRGEPGFPGVPGGTGPKGDRGETGSKGEQGLPG

ERGLRGEPGFPGVPGGTGPKGDRGETGSKGEQGLPGERGLRGEPGFPGVP

GGTGPKGDRGETGSKGEQGLPGERGLRGEPGFPGVPGGTGPKGDRGETGS

-continued

KGEQGLPGERGLRGEPGFPGVPGGTGPKGDRGETGSKGEQGLPGERGLRG

EPGFPGVPGGTGPKGDRGETGSKGEQGLPGERGLRGEP (2) The amino acid sequence of recombinant
type VII humanized collagen C7P11:
                                    (SEQ ID NO: 5)
GLTGPTGAVGLPGPPGPSGLVGPQGSPGLPGQVGETGKPGAPGRDGASGK

DGDRGSPGVPGSPGLPGPVGPKGEPGPTGAPGLTGPTGAVGLPGPPGPSG

LVGPQGSPGLPGQVGETGKPGAPGRDGASGKDGDRGSPGVPGSPGLPGPV

GPKGEPGPTGAPGLTGPTGAVGLPGPPGPSGLVGPQGSPGLPGQVGETGK

PGAPGRDGASGKDGDRGSPGVPGSPGLPGPVGPKGEPGPTGAPGLTGPTG

AVGLPGPPGPSGLVGPQGSPGLPGQVGETGKPGAPGRDGASGKDGDRGSP

GVPGSPGLPGPVGPKGEPGPTGAP (3) The amino acid sequence of recombinant
type VII humanized collagen C7P12:
                                    (SEQ ID NO: 6)
GEPGAKGDRGLPGPRGEKGEAGRAGEPGDPGEDGQKGAPGPKGFKGDPGE

PGAKGDRGLPGPRGEKGEAGRAGEPGDPGEDGQKGAPGPKGFKGDPGEPG

AKGDRGLPGPRGEKGEAGRAGEPGDPGEDGQKGAPGPKGFKGDPGEPGAK

GDRGLPGPRGEKGEAGRAGEPGDPGEDGQKGAPGPKGFKGDPGEPGAKGD

RGLPGPRGEKGEAGRAGEPGDPGEDGQKGAPGPKGFKGDPGEPGAKGDRG

LPGPRGEKGEAGRAGEPGDPGEDGQKGAPGPKGFKGDP.

7. It has been optimized for the codons of *E. coli* in the present application, and the optimized base sequences are as follows.

(1) The base sequence for the recombinant
type VII humanized collagen C7P7 is
                                    (SEQ ID NO: 7)
GGATTTCCCGGGGTCCCGGGAGGCACCGGCCCTAAAGGCGATCGTGGTGA

AACCGGCAGCAAGGGCGAGCAGGGTCTGCCGGGCGAGCGCGGTTTGAGAG

GCGAACCGGGTTTTCCAGGCGTGCCGGGCGGTACGGGTCCGAAGGGTGAC

CGTGGCGAAACCGGCAGCAAGGGTGAACAAGGTTTACCGGGTGAACGCGG

TCTGCGTGGTGAGCCGGGCTTCCCAGGTGTTCCGGGCGGAACCGGTCCTA

AAGGTGATCGTGGCGAAACCGGTTCCAAAGGCGAACAAGGTCTTCCGGGT

GAGCGCGGTCTGCGTGGCGAACCGGGTTTCCCGGGCGTGCCGGGAGGCAC

CGGCCCAAAGGGCGACCGCGGAGAAACCGGCAGCAAAGGCGAGCAGGGCC

TGCCGGGTGAACGTGGCCTGCGTGGTGAGCCGGGATTCCCGGGTGTTCCG

GGCGGCACCGGTCCGAAAGGTGATCGTGGTGAAACCGGTAGCAAGGGTGA

ACAGGGTCTGCCGGGCGAGCGCGGCTTGAGAGGTGAGCCTGGTTTTCCGG

GGGTGCCCGGCGGTACGGGCCCGAAAGGCGACCGTGGCGAAACCGGTTCT

AAGGGTGAGCAGGGTCTGCCGGGTGAGCGTGGTCTGCGCGGTGAGCCGGG

TTTCCCGGGCGTTCCGGGTGGCACTGGTCCGAAGGGCGACCGTGGCGAGA

CTGGCTCGAAAGGTGAACAGGGTTTGCCGGGTGAGCGTGGTCTGCGTGGT

GAGCCGGGTTTTCCGGGCGTGCCGGGTGGCACGGGCCCAAAAGGCGATCG

TGGTGAGACCGGTTCCAAGGGCGAGCAAGGTCTGCCGGGCGAGCGCGGTC

TCCGCGGTGAACCG;

-continued (2) the base sequence for the recombinant
type VII humanized collagen C7P11 is:
                                    (SEQ ID NO: 8)
GGACTAACAGGGCCGACCGGTGCGGTCGGCCTGCCGGGACCACCGGGCCC

CAGCGGTCTGGTTGGTCCTCAGGGTTCCCCGGGTCTTCCGGGCCAGGTTG

GTGAGACAGGCAAGCCGGGTGCGCCGGGCCGTGACGGTGCCTCTGGTAAA

GACGGCGATCGTGGTTCGCCGGGCGTTCCGGGTTCGCCGGGTCTGCCGGG

TCCGGTCGGTCCGAAAGGTGAACCGGGGCCCACTGGTGCGCCAGGCTTGA

CCGGTCCGACCGGTGCGGTTGGCCTCCCGGGCCCACCGGGACCGAGCGGT

CTGGTTGGCCCACAAGGTTCCCCGGGCTTACCGGGCCAGGTTGGAGAAAC

CGGTAAGCCGGGTGCACCGGGGCGCGACGGCGCAAGCGGTAAGGACGGCG

ACCGCGGTAGCCCGGGCGTGCCGGGTAGCCCGGGCCTGCCGGGCCCGGTG

GGCCCCAAGGGTGAGCCGGGACCGACCGGCGCTCCGGGGTTGACCGGTCC

AACGGGCGCTGTGGGCCTGCCGGGTCCACCGGGTCCGAGCGGTCTGGTTG

GCCCGCAGGGTAGCCCGGGTCTGCCGGGCCAAGTTGGTGAAACCGGTAAA

CCGGGAGCACCAGGCCGTGATGGTGCCTCCGGTAAGGACGGCGATCGCGG

TTCTCCGGGCGTCCCGGGCTCCCCGGGTCTGCCGGGCCCGGTGGGTCCGA

AAGGTGAGCCGGGCCCGACGGGCGCGCCGGGCTTGACCGGCCCGACGGGT

GCTGTGGGTCTGCCGGGCCCTCCGGGTCCAAGCGGTCTGGTGGGCCCTCA

AGGTTCTCCGGGTCTGCCGGGACAGGTGGGCGAAACCGGTAAGCCGGGTG

CGCCAGGTCGTGATGGCGCGAGCGGCAAAGATGGTGATCGTGGCAGTCCG

GGGGTGCCGGGCAGCCCGGGCTTGCCGGGTCCAGTAGGTCCGAAAGGCGA

GCCGGGCCCGACCGGCGCGCCT;
and (3) the base sequence for the recombinant
type VII humanized collagen C7P12 is:
                                    (SEQ ID NO: 9)
GGAGAACCCGGGGCGAAGGGCGACCGCGGTCTGCCGGGTCCGCGTGGTGA

AAAAGGTGAGGCGGGCCGCGCAGGCGAACCGGGTGACCCGGGCGAGGATG

GTCAGAAAGGCGCGCCAGGTCCGAAAGGTTTTAAAGGCGATCCGGGCGAA

CCGGGTGCCAAGGGCGATAGAGGTCTGCCGGGTCCGCGTGGCGAAAAGGG

TGAAGCGGGTCGTGCGGGTGAACCGGGTGACCCGGGCGAGGACGGTCAGA

AGGGCGCGCCAGGTCCGAAAGGCTTCAAAGGTGACCCGGGTGAACCGGGC

GCGAAAGGCGACCGTGGTTTACCGGGTCCGCGTGGTGAGAAGGGGGAGGC

TGGTCGTGCCGGTGAACCGGGCGACCCAGGCGAGGATGGTCAGAAAGGCG

CGCCTGGTCCCAAGGGCTTCAAGGGCGACCCGGGTGAACCGGGTGCCAAA

GGGGATCGCGGTTTGCCAGGTCCTCGCGGTGAAAAGGGCGAGGCTGGTCG

CGCTGGTGAGCCGGGCGACCCGGGTGAAGATGGTCAAAAAGGCGCTCCGG

GTCCGAAGGGTTTTAAAGGTGATCCGGGCGAGCCGGGTGCGAAGGGCGAT

CGTGGCCTGCCGGGCCCACGTGGTGAGAAAGGCGAGGCCGGTCGTGCAGG

CGAACCGGGTGACCCCGGCGAAGATGGCCAAAAGGGTGCGCCTGGCCCGA

AGGGATTCAAAGGCGATCCGGGTGAGCCGGGCGCGAAAGGCGACCGCGGC

CTGCCGGGTCCGCGTGGTGAGAAGGGCGAGGCAGGCCGTGCAGGTGAACC

-continued

GGGTGACCCGGGTGAGGATGGTCAAAAAGGTGCTCCGGGTCCGAAGGGCT

TTAAGGGCGACCCG.

The amino acid sequence of the recombinant type VII humanized collagen prepared in the present application is derived from the functional region of human natural type VII collagen, and comprises the functional region and a similar functional region, as well as proteins with amino acid sequence mutated and modified respectively.

The application field of the recombinant type VII humanized collagen prepared in the present application includes the preparation of high-end medical devices, such as biological dressings, human body biomimetic materials, materials for plastic surgery and aesthetics, organoid culture, tissue injection and filling, skin repair and regeneration, oral mucosa repair and regeneration, cervical mucosa repair and regeneration, gynaecology and obstetrics biological materials, 3D printing artificial organ biological materials, etc.; high-end cosmetic raw materials, and high-end medicinal auxiliary materials; and food additives, etc.

The advantages of the present application include:
1. The present application provides the core functional region and amino acid sequence of recombinant type VII humanized collagen.
2. The present application successfully biosynthesized recombinant type VII humanized collagen for the first time.
3. The recombinant type VII humanized collagen prepared in the present application has a good effect of cell adhesion and a good effect of promoting cell proliferation, and it does not cause an immune response when applied to the human body.
4. The preparation method is simple and the recombinant type VII humanized collagen may be obtained on a large scale.
5. The excellent performance of the recombinant type VII humanized collagen makes it expected to be widely applied in fields such as biological dressings, human body biomimetic materials, materials for plastic surgery and aesthetics, organoid culture, tissue injection and filling, skin repair and regeneration, oral mucosa repair and regeneration, cervical mucosa repair and regeneration, gynaecology and obstetrics biological materials, 3D printing artificial organ biological materials, etc.; high-end cosmetic raw materials, and high-end medicinal auxiliary materials; and food additives, etc.

DETAILED DESCRIPTION

Figure 1:
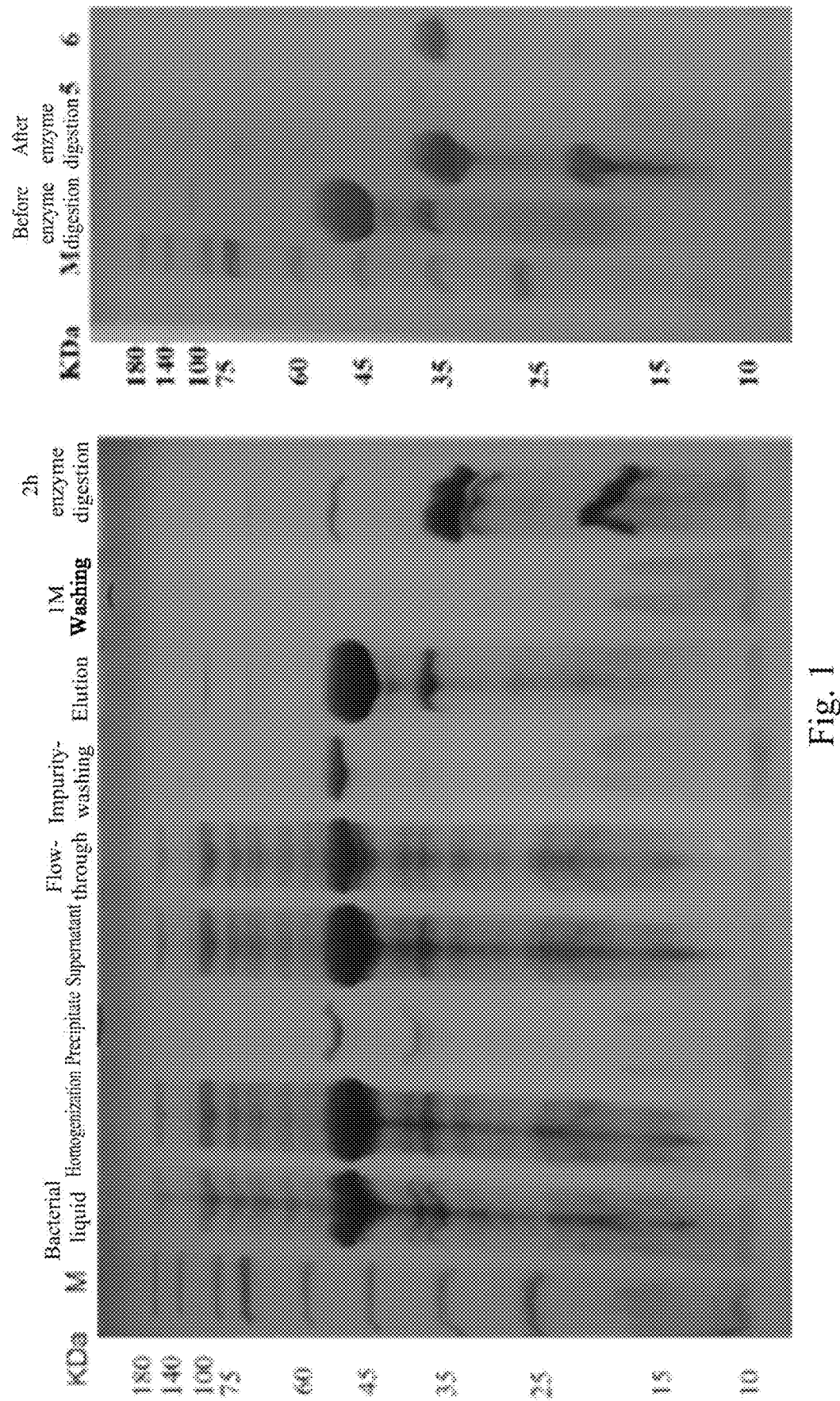
FIG. 1: The purification of recombinant type VII humanized collagen C7P7 (5, no sample loaded; 6, the loaded flow-through sample collected in fine purification, which is the target protein).

In order to make the purpose, technical solutions, and advantages of the present application clearer, the technical solutions in the embodiments of the present application will be clearly and completely described below in combination with the embodiments of the present application. It is obvious that the described embodiments are a part of, but not all the embodiments of the present application. Based on the embodiments in the present application, all other embodiments obtained by those of ordinary skilled in the art without creative work fall within the scope of protection of the present application.

As used herein, a polypeptide refers to a plurality of amino acid residues linked by peptide bonds. Herein, a polypeptide comprises a plurality of repeating units derived from human type VII collagen. A polypeptide may comprise (repeating unit)$_n$, and the repeating unit comprises the amino acid sequence of SEQ ID NO. 1. Herein, each repeating unit may be directly linked or may be separated by one or more amino acid residues. The number n of the repeating units may be 4-20, such as 5, 6, 7, 8, 9, 10, 11, 12, 13, 14, 15, 16, 17, 18 or 19. The concentration of the polypeptide may be more than 1 mg/ml, more than 5 mg/ml, more than 10 mg/ml, or more than 12 mg/ml.

Herein, the repeating unit of the present application may comprise or be a sequence of

```
                                            (SEQ ID NO: 1)
GFPGVPGGTGPKGDRGETGSKGEQGLPGERGLRGEP;

(SEQ ID NO: 2)
GLTGPTGAVGLPGPPGPSGLVGPQGSPGLPGQVGETGKPGAPGRDGASGK

DGDRGSPGVPGSPGLPGPVGPKGEPGPTGAP;
or (SEQ ID NO: 3)
GEPGAKGDRGLPGPRGEKGEAGRAGEPGDPGEDGQKGAPGPKGFKGDP.
```

As used herein, "nucleic acid" refers to a plurality of nucleotides linked by internucleotide linkage. The internucleotide linkage may be, for example, a phosphodiester linkage. The nucleic acid herein may comprise a polynucleotide encoding a polypeptide of the present application. In order to facilitate the subsequent processing of the polypeptide, the nucleic acid of the present application may also comprise nucleotides encoding a purification tag, such as an His tag, a GST tag, an MBP tag, a SUMO tag or a Nus tag, and a nucleotide sequence encoding a leader sequence when needed.

As used herein, the term "vector" is a nucleic acid carrier tool into which a polynucleotide is inserted. When a vector allows the expression of the protein encoded by the inserted polynucleotide, the vector is called an expression vector. The vector may be introduced into a host cell through either transformation, transduction, or transfection, so that the genetic material elements it carries may be expressed in the host cell. The vector is well known to those skilled in the art, including but not limited to: plasmids; phagemids; cosmids; artificial chromosomes such as yeast artificial chromosomes (YAC), bacterial artificial chromosomes (BAC) or P1-derived artificial chromosomes (PAC); phages such as lambda phages or M13 phages; and animal viruses, and the like. The vector may contain a variety of elements for controlling expression, including but not limited to promoter sequences, transcription initiation sequences, enhancer sequences, selection elements, and reporter genes. In addition, the vector may also contain an origin of replication. The vector may comprise the nucleic acid of the present application to facilitate introduction into a cell for expression. The vector may comprise an expression control element, such as a promoter, a terminator, and/or an enhancer operably linked to said nucleic acid.

As used herein, the term "host cell" is a cell into which a nucleic acid molecule has been introduced by molecular biology techniques. These techniques include transfection with viral vectors, transformation with plasmid vectors, and introduction of naked DNA by electroporation, lipofection, and particle gun acceleration. The host cell may be a eukaryotic cell or a prokaryotic cell. The eukaryotic cell is, for example, a yeast cell, an animal cell and/or an insect cell. The prokaryotic cell may be an *E. coli* cell.

Herein, the repeating unit of the polypeptide or the polypeptide of the present application may have certain mutations. For example, the amino acid sequence of one or more of these portions may have a substitution, deletion, addition or insertion of amino acid residue. That is, repeating unit variants may be used in the present application, provided that the variants retain the activity in promoting cell adhesion and/or proliferation. Specifically, a variant may have a certain percent identity, such as 80%, 85%, 90%, 91%, 92%, 93%, 94%, 95%, 96%, 97%, 98%, and 99% identity to a specified sequence. The specified sequence may be any sequence of the present application, such as SEQ ID NOs. 1-6, but it is preferred that these variants retain the core sequence identified in the present application.

The polypeptides of the present application may be prepared by any suitable means, for example, by synthesis. Preferably, the polypeptide of the present application may be prepared by recombinant means.

The polypeptide, nucleic acid, vector and/or host cell of the present application may be prepared into a composition or a kit. The composition or kit may comprise one or more of biological dressings, human body biomimetic materials, materials for plastic surgery and aesthetics, organoid culture materials, cardiovascular stent materials, coating materials, tissue injection and filling materials, ophthalmic materials, gynaecology and obstetrics biological materials, nerve repair and regeneration materials, liver tissue materials and vascular repair and regeneration materials, 3D printing artificial organ biomaterials, cosmetic raw materials, medicinal auxiliary materials and food additives. The composition may be one or more of biological dressings, human body biomimetic materials, materials for plastic surgery and aesthetics, organoid culture materials, cardiovascular stent materials, coating materials, tissue injection and filling materials, ophthalmic materials, gynaecology and obstetrics biological materials, nerve repair and regeneration materials, liver tissue materials and vascular repair and regeneration materials, 3D printing artificial organ biomaterials, cosmetic raw materials, medicinal auxiliary materials and food additives. The composition or kit may be used to promote cell adhesion or proliferation in vitro or in vivo.

The present application discloses a specific process of functional region screening and synthesis process of recombinant type VII humanized collagen, which may be used as human body structural material preparation. The present application belongs to the field of synthetic biotechnology. The biosynthetic method for preparing recombinant type VII humanized collagen in the present application comprises the following specific processes: (1) functional region screening and strain construction; (2) biological fermentation, induction and expression; (3) purification and optional enzyme digestion of the humanized type VII collagen. The amino acid sequence of the recombinant humanized collagen prepared in the present application is derived from the functional region of human natural type VII collagen, and comprises the functional region and a similar functional region, and proteins with amino acid sequence mutated and modified respectively. The recombinant type VII humanized collagen prepared in the application has a high activity of promoting cell adhesion or activity of promoting cell proliferation and does not produce an immune response when applied to a human body. The preparation method of the recombinant type VII humanized collagen is novel. The recombinant type VII humanized collagen can be obtained on a large scale, and is widely applied in the preparation of human structural materials. The application fields include the preparation of high-end medical devices, such as biological dressings, human body biomimetic materials, materials for plastic surgery and aesthetics, organoid culture, tissue injection and filling, skin repair and regeneration, oral mucosa repair and regeneration, cervical mucosa repair and regeneration, gynaecology and obstetrics biological materials, 3D printing artificial organ biological materials; high-end cosmetic raw materials, and high-end medicinal auxiliary materials; and food additives and the like

EXAMPLES

The following Examples are provided to illustrate the present application. Those skilled in the art should understand that the examples are merely illustrative but not limiting. The present application is limited only by the scope of the appended claims.

Example 1 Construction and Expression of Recombinant Type VII Humanized Collagen Large-scale functional region screening was conducted to obtain the following different target gene segments of recombinant type VII humanized collagen:

```
(1) the amino acid sequence of recombinant
humanized type VII collagen C7P7
(SEQ ID NO: 4):
GFPGVPGGTGPKGDRGETGSKGEQGLPGERGLRGEPGFPGVPGGTGPKGD

RGETGSKGEQGLPGERGLRGEPGFPGVPGGTGPKGDRGETGSKGEQGLPG

ERGLRGEPGFPGVPGGTGPKGDRGETGSKGEQGLPGERGLRGEPGFPGVP

GGTGPKGDRGETGSKGEQGLPGERGLRGEPGFPGVPGGTGPKGDRGETGS

KGEQGLPGERGLRGEPGFPGVPGGTGPKGDRGETGSKGEQGLPGERGLRG

EPGFPGVPGGTGPKGDRGETGSKGEQGLPGERGLRGEP;

(2) the amino acid sequence of recombinant
humanized type VII collagen C7P11
(SEQ ID NO: 5):
GLTGPTGAVGLPGPPGPSGLVGPQGSPGLPGQVGETGKPGAPGRDGASGK

DGDRGSPGVPGSPGLPGPVGPKGEPGPTGAPGLTGPTGAVGLPGPPGPSG

LVGPQGSPGLPGQVGETGKPGAPGRDGASGKDGDRGSPGVPGSPGLPGPV

GPKGEPGPTGAPGLTGPTGAVGLPGPPGPSGLVGPQGSPGLPGQVGETGK
```

-continued

```
PGAPGRDGASGKDGDRGSPGVPGSPGLPGPVGPKGEPGPTGAPGLTGPTG

AVGLPGPPGPSGLVGPQGSPGLPGQVGETGKPGAPGRDGASGKDGDRGSP

GVPGSPGLPGPVGPKGEPGPTGAP
```

(3) the amino acid sequence of recombinant
humanized type VII collagen C7P12
(SEQ ID NO: 6):
```
GEPGAKGDRGLPGPRGEKGEAGRAGEPGDPGEDGQKGAPGPKGFKGDPGE

PGAKGDRGLPGPRGEKGEAGRAGEPGDPGEDGQKGAPGPKGFKGDPGEPG

AKGDRGLPGPRGEKGEAGRAGEPGDPGEDGQKGAPGPKGFKGDPGEPGAK

GDRGLPGPRGEKGEAGRAGEPGDPGEDGQKGAPGPKGFKGDPGEPGAKGD

RGLPGPRGEKGEAGRAGEPGDPGEDGQKGAPGPKGFKGDPGEPGAKGDRG

LPGPRGEKGEAGRAGEPGDPGEDGQKGAPGPKGFKGDP;
```

(4) the base sequence of the recombinant
type VII humanized collagen C7P7 is
(SEQ ID NO: 7):
```
GGATTTCCCGGGGTCCCGGGAGGCACCGGCCCTAAAGGCGATCGTGGTGA

AACCGGCAGCAAGGGCGAGCAGGGTCTGCCGGGCGAGCGCGGTTTGAGAG

GCGAACCGGGTTTTCCAGGCGTGCCGGGCGGTACGGGTCCGAAGGGTGAC

CGTGGCGAAACCGGCAGCAAGGGTGAACAAGGTTTACCGGGTGAACGCGG

TCTGCGTGGTGAGCCGGGCCTTCCCAGGTGTTCCGGGCGGAACCGGTCCTA

AAGGTGATCGTGGCGAAACCGGTTCCAAAGGCGAACAAGGTCTTCCGGGT

GAGCGCGGTCTGCGTGGCGAACCGGGTTTCCCGGGCGTGCCGGGAGGCAC

CGGCCCAAAGGGCGACCGCGGAGAAACCGGCAGCAAAGGCGAGCAGGGCC

TGCCGGGTGAACGTGGCCTGCGTGGTGAGCCGGGATTCCCGGGTGTTCCG

GGCGGCACCGGTCCGAAAGGTGATCGTGGTGAAACCGGTAGCAAGGGTGA

ACAGGGTCTGCCGGGCGAGCGCGGCTTGAGAGGTGAGCCTGGTTTTCCGG

GGGTGCCCGGCGGTACGGGCCCGAAAGGCGACCGTGGCGAAACCGGTTCT

AAGGGTGAGCAGGGTCTGCCGGGTGAGCGTGGTCTGCGCGGTGAGCCGGG

TTTCCCGGGCGTTCCGGGTGGCACTGGTCCGAAGGGCGACCGTGGCGAGA

CTGGCTCGAAAGGTGAACAGGGTTTGCCGGGTGAGCGTGGTCTGCGTGGT

GAGCCGGGTTTTCCGGGCGTGCCGGGTGGCACGGGCCCAAAAGGCGATCG

TGGTGAGACCGGTTCCAAGGGCGAGCAAGGTCTGCCGGGCGAGCGCGGTC

TCCGCGGTGAACCG;
```

(5) the base sequence of the recombinant
type VII humanized collagen C7P11 is
(SEQ ID NO: 8):
```
GGACTAACAGGGCCGACCGGTGCGGTCGGCCTGCCGGGACCACCGGGCCC

CAGCGGTCTGGTTGGTCCTCAGGGTTCCCCGGGTCTTCCGGGCCAGGTTG

GTGAGACAGGCAAGCCGGGTGCGCCGGGCCGTGACGGTGCCTCTGGTAAA

GACGGCGATCGTGGTTCGCCGGGCGTTCCGGGTTCGCCGGGTCTGCCGGG

TCCGGTCGGTCCGAAAGGTGAACCGGGGCCCACTGGTGCGCCAGGCTTGA

CCGGTCCGACCGGTGCGGTTGGCCTCCCGGGCCCACCGGGACCGAGCGGT

CTGGTTGGCCCACAAGGTTCCCCGGGCTTACCGGGCCAGGTTGGAGAAAC

CGGTAAGCCGGGTGCACCGGGGCGCGACGGCGCAAGCGGTAAGGACGGCG

ACCGCGGTAGCCCGGGCGTGCCGGGTAGCCCGGGCCTGCCGGGCCCGGTG
```

-continued

```
GGCCCCAAGGGTGAGCCGGGACCGACCGGCGCTCCGGGGTTGACCGGTCC

AACGGGCGCTGTGGGCCTGCCGGGTCCACCGGGTCCGAGCGGTCTGGTTG

GCCCGCAGGGTAGCCCGGGTCTGCCGGGCCAAGTTGGTGAAACCGGTAAA

CCGGGAGCACCAGGCCGTGATGGTGCCTCCGGTAAGGACGGCGATCGCGG

TTCTCCGGGCGTCCCGGGCTCCCCGGGTCTGCCGGGCCCGGTGGGTCCGA

AAGGTGAGCCGGGCCCGACGGGCGCGCCGGGCTTGACCGGCCCGACGGGT

GCTGTGGGTCTGCCGGGCCCTCCGGGTCCAAGCGGTCTGGTGGGCCCTCA

AGGTTCTCCGGGTCTGCCGGGACAGGTGGGCGAAACCGGTAAGCCGGGTG

CGCCAGGTCGTGATGGCGCGAGCGGCAAAGATGGTGATCGTGGCAGTCCG

GGGGTGCCGGGCAGCCCGGGCTTGCCGGGTCCAGTAGGTCCGAAAGGCGA

GCCGGGCCCGACCGGCGCGCCT;
```

(6) the base sequence of the recombinant
type VII humanized collagen C7P12 is
(SEQ ID NO: 9):
```
GGAGAACCCGGGCGAAGGGCGACCGCGGTCTGCCGGGTCCGCGTGGTGA

AAAAGGTGAGGCGGGCCGCGCAGGCGAACCGGGTGACCCGGGCGAGGATG

GTCAGAAAGGCGCGCCAGGTCCGAAAGGTTTTAAAGGCGATCCGGGCGAA

CCGGGTGCCAAGGGCGATAGAGGTCTGCCGGGTCCGCGTGGCGAAAAGGG

TGAAGCGGGTCGTGCGGGTGAACCGGGTGACCCGGGCGAGGACGGTCAGA

AGGGCGCGCCAGGTCCGAAAGGCTTCAAAGGTGACCCGGGTGAACCGGGC

GCGAAAGGCGACCGTGGTTTACCGGGTCCGCGTGGTGAGAAGGGGGAGGC

TGGTCGTGCCGGTGAACCGGGCGACCCAGGCGAGGATGGTCAGAAAGGCG

CGCCTGGTCCCAAGGGCTTCAAGGGCGACCCGGGTGAACCGGGTGCCAAA

GGGGATCGCGGTTTGCCAGGTCCTCGCGGTGAAAAGGGCGAGGCTGGTCG

CGCTGGTGAGCCGGGCGACCCGGGTGAAGATGGTCAAAAAGGCGCTCCGG

GTCCGAAGGGTTTTAAAGGTGATCCGGGCGAGCCGGGTGCGAAGGGCGAT

CGTGGCCTGCCGGGCCCCACGTGGTGAGAAAGGCGAGGCCGGTCGTGCAGG

CGAACCGGGTGACCCCGGCGAAGATGGCCAAAAGGGTGCGCCTGGCCCGA

AGGGATTCAAAGGCGATCCGGGTGAGCCGGGCGCGAAAGGCGACCGCGGC

CTGCCGGGTCCGCGTGGTGAGAAGGGCGAGGCAGGCCGTGCAGGTGAACC

GGGTGACCCGGGTGAGGATGGTCAAAAAGGTGCTCCGGGTCCGAAGGGCT

TTAAGGGCGACCCG.
```

2. The synthesized gene segment was inserted into a pET-28a-Trx-His expression vector to obtain a recombinant expression plasmid.

3. The successfully constructed expression plasmid was transformed into *E. coli* competent cells BL21 (DE3). The specific processes were as follows. (1) The *E. coli* competent cells BL21 (DE3) in an ultra-low temperature refrigerator were taken out and placed on ice; 2 μl of the plasmid to be transformed was added to the *E. coli* competent cells BL21 (DE3) when half melted, and mixed slightly for 2-3 times. (2) The mixture was placed on ice for an ice bath of 30 min, then heat shocked by a water bath at 42° C. for 45-90 seconds, and taken out followed by placed on ice for an ice bath of 2 min. (3) The mixture was transferred to a biosafety cabinet and added with 700 μl LB liquid culture medium, then cultured at 37° C., 220 rpm for 60 min.

(4) 200 μl of bacterial liquid was taken and evenly spread on an LB plate containing kanamycin sulfate. (5) The plate was cultured in an incubator at 37° C. for 15-17 h until colonies of uniform size grow.

4. 5-6 single colonies were picked from the transformed LB plate to shake flasks containing antibiotic (kanamycin sulfate) stock solution, and placed in a constant temperature shaker at 220 rpm and 37° C. for 7 h. Then the cultured shake flasks were cooled to 16° C., and added with IPTG to induce expression for a period of time. Then samples were taken for electrophoresis detection (as shown by the lanes "Bacterial liquid" in FIGS. 1-3), and the bacterial liquid was divided into centrifuge bottles and centrifuged at 8000 rpm and 4° C. for 10 min. Then the bacterial cells were collected and the weight of the bacterial cells was recorded.

5. The collected bacterial cells were resuspended in a balanced working buffer, and the bacterial liquid was cooled to ≤15° C., and homogenized through high-pressure homogenization twice. After completion, the bacterial liquid was collected (as shown by lanes "Homogenization" in FIGS. 1-3). The homogenized bacterial liquid was dispensed into centrifuge bottles, and centrifuged at 17000 rpm and 4° C. for 30 min. The supernatant was collected, and the supernatant and precipitate were taken for electrophoresis detection (as shown by lanes "Supernatant" and "Precipitate" in FIGS. 1-3).

Figure 2:
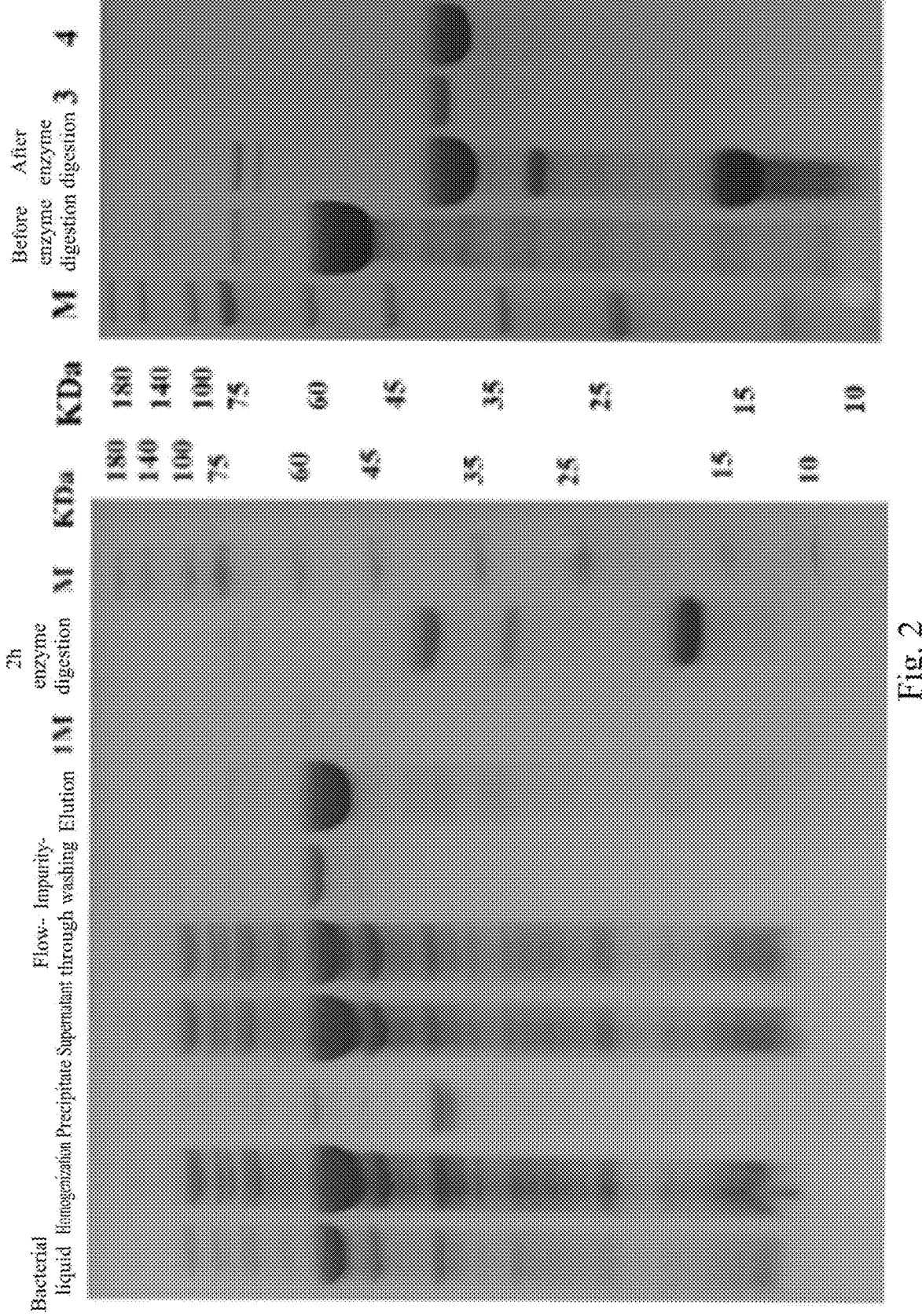
FIG. 2: The purification of recombinant type VII humanized collagen C7P11 (3 and 4, the loaded flow-through sample collected in fine purification, which is the target protein).
Figure 3:
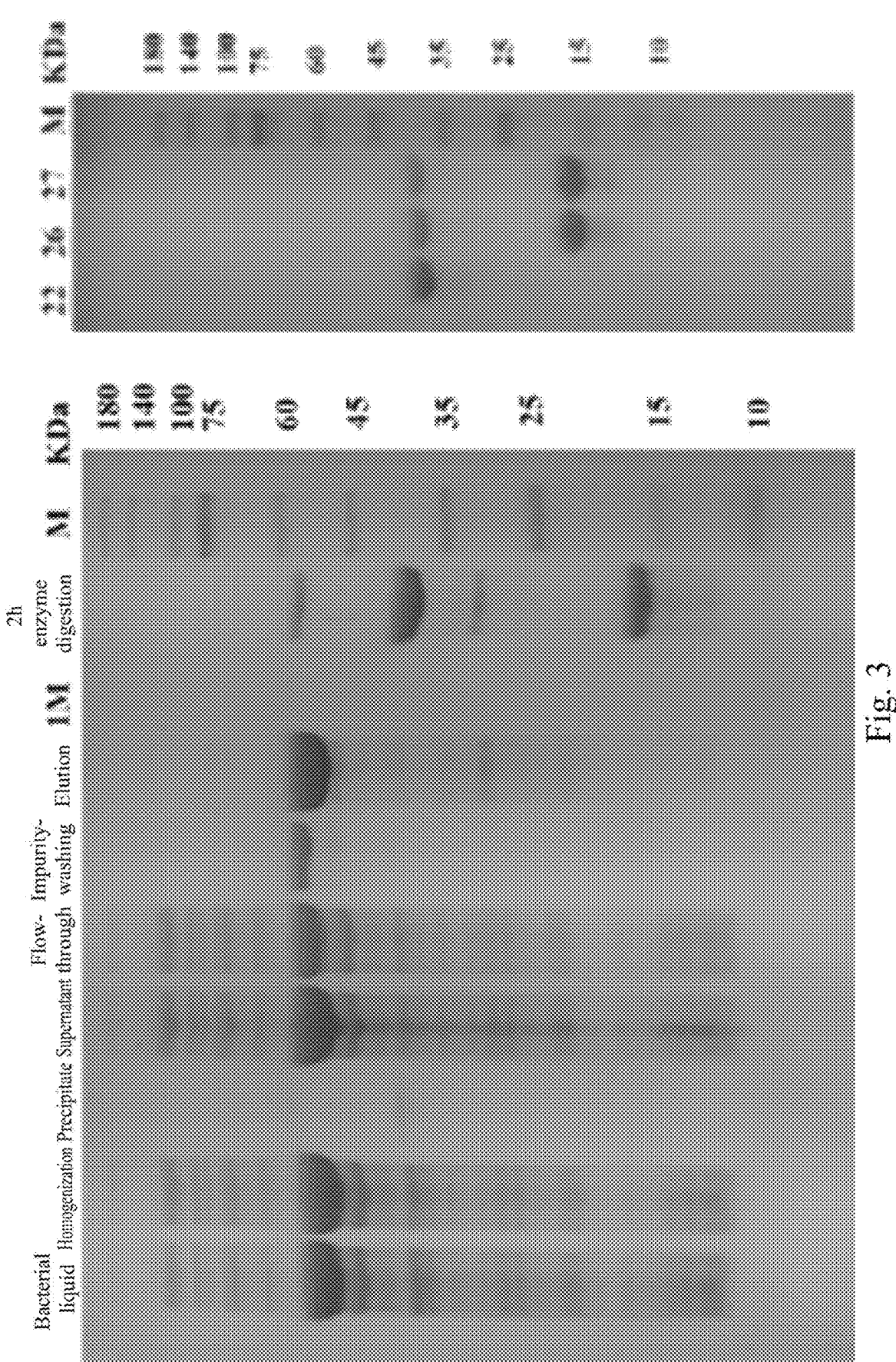
FIG. 3: The purification of recombinant type VII humanized collagen C7P12 (22, the loaded flow-through sample is collected in fine purification, which is the target protein; 26, the protein post enzyme digestion; 27, the protein post buffer exchange).

6. The recombinant humanized type VII collagen was purified and enzymatically digested. The specific processes were as follows. (1) Crude purification: a. washing the column material with water; b. equilibrating the column material with equilibration buffer (200 mM sodium chloride, 25 mM Tris, 20 mM imidazole); c. sample loading: adding the centrifuged supernatant to the column until the liquid drained completely, and the flow-through was taken for electrophoresis test (as shown by lanes "Flow-through" in FIGS. 1-3); d. washing of impure proteins: adding 25 mL of washing buffer (200 mM sodium chloride, 25 mM Tris, 20 mM imidazole) until the liquid drained completely, and the impurity-washing flow-through was taken for electrophoresis testing (as shown by lanes "Impurity-washing" in FIGS. 1-3); e. collection of the target protein: adding 20 mL of elution buffer (200 mM sodium chloride, 25 mM Tris, 250 mM imidazole) and collecting the flow-through, then detecting the protein concentration using UV-visible spectrophotometry with a calculation of the protein concentration according to the following formula (C (mg/ml)=A280×dilution fold×extinction coefficient); and conducting an electrophoresis detection (as shown by lanes "Elution" in FIGS. 1-3); f. washing the column with IM imidazole working buffer (as shown by lanes "1M Washing" in FIGS. 1-3). And g. washing the column material with purified water. (2) Enzyme digestion (as shown by lanes "After enzyme digestion" in FIGS. 1-3): adding TEV enzyme at a 20:1 ratio of the total amount of proteins to the total amount of TEV enzymes for enzyme digestion at 16° C. for 2 hours, to obtain the target protein, and sampling for electrophoresis detection. The solution of the enzymatically digested protein was put into a dialysis bag, dialyzed at 4° C. for 2 hours, and then transferred into new dialysate for dialysis at 4° C. overnight. (3) Fine purification: a. column material equilibration: equilibrating the column material by using A buffer (20 mM Tris, 20 mM sodium chloride) with a flow rate of 10 ml/min; b. sample loading: loading the sample and collecting the flow-through with a flow rate of 5 ml/min, obtaining recombinant type VII humanized collagen C7P7, C7P11 and C7P12, and performing electrophoresis detection. Lane 6 of FIG. 1 shows the apparent molecular weight of recombinant type VII humanized collagen C7P7, which is generally consistent with the predicted molecular weight of 27.8 kDa. Lanes 3 and 4 of FIG. 2 show the apparent molecular weight of recombinant type VII humanized collagen C7P11, which is generally consistent with the predicted molecular weight of 28.5 kDa. Lane 26 of FIG. 3 shows the apparent molecular weight of recombinant VII humanized collagen C7P12, which is generally consistent with the predicted molecular weight of 27.5 kDa. In order to further confirm the identity of the isolated C7P7, C7P11 and C7P12, the inventors performed mass spectrometry detection of recombinant type VII humanized collagen in Example 3.

Example 2 Detection of the Activity of Recombinant Type VII Humanized Collagen in Promoting Cell Proliferation The method for detecting the activity of collagen in promoting cell proliferation may refer to Pharmaceutical industry standard of the People's Republic of China YYT 1849-2022 recombinant collagen. The specific implementation method was as follows.

(1) The principle of the method is that: CCK8 reagent contains WST-8[chemical name: 2-(2-methoxy-4-nitrophenyl)-3-(4-nitrophenyl)-5-(2,4-disulfonic acid benzene)-2H-tetrazole monosodium salt], which is reduced to a highly water-soluble yellow formazan product (Formazan dye) by dehydrogenase in cells under the action of electron carrier 1-methoxy-5-methylphenazinium dimethyl sulfate (1-Methoxy PMS). The amount of formazan generated is directly proportional to the number of living cells. Therefore, this characteristic can be used to perform cell proliferation and toxicity analysis directly.

(2) Experimental grouping: complete medium DMEM was used as a negative control, 8% NaCl was used as a positive control, collagen solution (solution in 8% NaCl) was used as a test sample, and complete culture medium without cells was used as zeroing well.

(3) Sample preparation: collagen was dissolved in the complete medium to the highest concentration, filtered and sterilized with a 0.22 μm microporous filter membrane, and prepared at each concentration. NaCl was dissolved in the complete medium to a final concentration of 8%, filtered, and sterilized.

(4) Cell plating: digestion with trypsin and counting were performed when the confluence of NIH 3T3 cells was around 90%. Cells were plated in a 96-well plate at a density of $(5\text{-}10)\times10^3$ cells per well, and the edge wells were sealed by adding 100 μL PBS. The cells were cultured for 24 h for adhesion.

(5) Application to cells: the supernatant was aspirated and discarded after cell adhesion, and the solutions of respective groups were replaced in turn with 4 replicate wells per group. The culture was cultured for 48 h.

(6) Experimental detection: the culture medium was discarded, and 100 μL (including 5 μL CCK8 solution) of basal culture medium was added. The culture was incubated in an incubator for 1-2 h and detected at a wavelength of 450 using an enzyme-linked immunosorbent assay reader. The formula for calculating cell viability was as follows.

Cell viability={(As–Ab)/(Ac–Ab)}×100%. Wherein, As was the absorbance of the recombinant collagen test well, Ab is the absorbance of the zeroing well, and Ac is the absorbance of the negative well.

Figure 4:
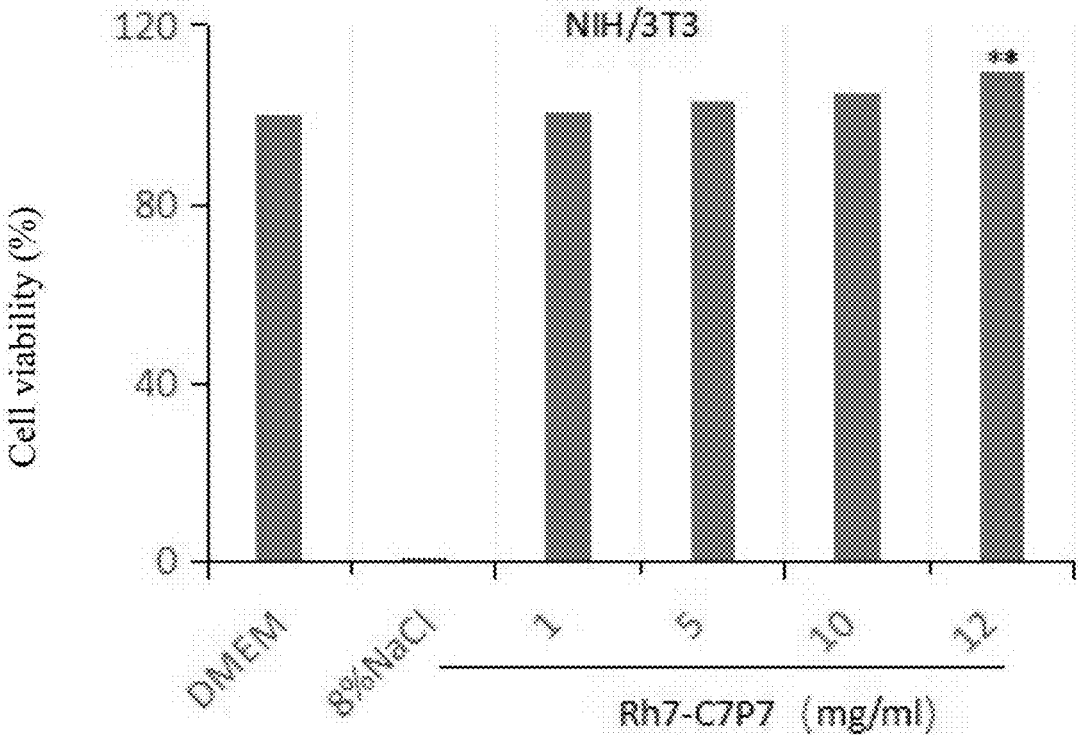
FIG. 4: The graph of the pro-proliferation effect of recombinant type VII humanized collagen C7P7.
Figure 5:
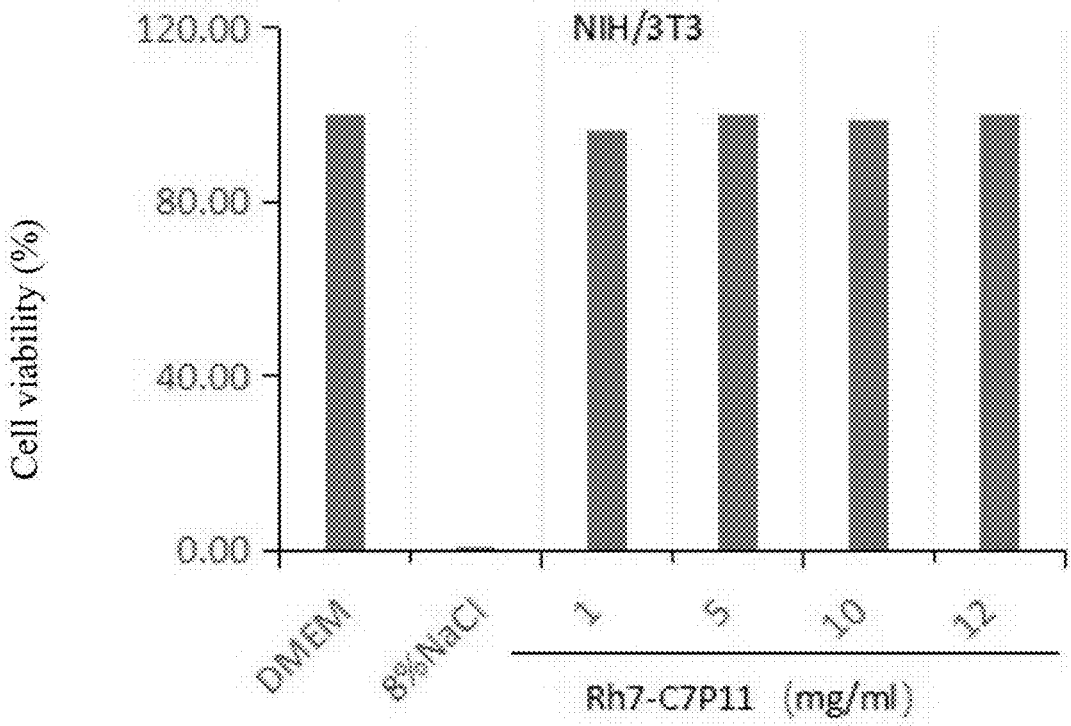
FIG. 5: The graph of the pro-proliferation effect of recombinant type VII humanized collagen C7P11.
Figure 6:
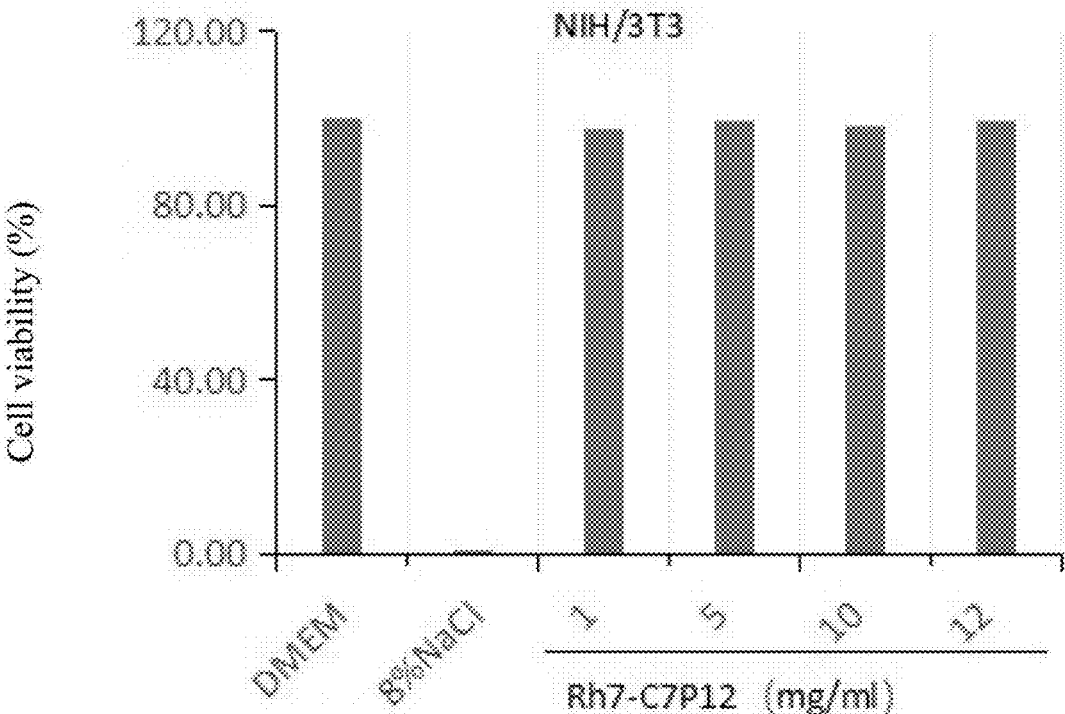
FIG. 6: The graph of the pro-proliferation effect of recombinant type VII humanized collagen C7P12.

FIG. 4 shows a graph of the pro-proliferation effect of recombinant type VII humanized collagen C7P7. FIG. 5 shows a graph of the pro-proliferation effect of recombinant type VII humanized collagen C7P11. FIG. 6 shows a graph of the pro-proliferation effect of recombinant type VII humanized collagen C7P12. As shown in FIGS. 4-6, the cell viability of the positive control group was zero compared with the negative control group, with a statistically significant difference. C7P7 exhibited a significant pro-proliferation effect at 12 mg/ml, while C7P11 and C7P12 had no promoting effect on cell proliferation. Unexpectedly, the inventors found that C7P7 can promote cell proliferation compared with C7P11 and C7P12, as evidenced by increased cell viability (see Table 1).

TABLE 1

Cell viability

| Tested samples | Cell viability (%) | | | |
| --- | --- | --- | --- | --- |
| | 1 mg/ml | 5 mg/ml | 10 mg/ml | 12 mg/ml |
| C7P7 | 100.84 | 103.12 | 105.10 | 109.80 |
| C7P11 | 96.48 | 99.79 | 99.03 | 100.32 |
| C7P12 | 97.48 | 99.31 | 98.03 | 99.32 |

Example 3 Mass Spectrometry Detection of Recombinant Type VII Humanized Collagen

Experimental Method

| Equipment name | Matrix-assisted laser desorption ionization-time of flight mass spectrometer, MALDI-TOF/TOF Ultraflextreme™, Brucker, Germany | | |
| --- | --- | --- | --- |
| Matrix | CHCA | Laser Energy | 125 |
| Data retrieval Software | Mascot | Retrieved Species | ALL entries |
| Search database | | NCBIprot | |

After the reduction with DTT and alkylation with iodo-acetamide, the protein sample was enzymatically digested overnight with trypsin. The peptide segments obtained after enzyme digestion were then desalted by C18ZipTip, mixed with the matrix α-cyano-4-hydroxycinnamic acid (CHCA), and spotted on plates. Finally, analysis was performed using the matrix-assisted laser desorption ionization-time of flight mass spectrometer MALDI-TOF/TOF Ulraflextreme™, Brucker, Germany (the technology of peptide fingerprinting referred to Protein J.2016;35:212-7). Data retrieval was handled via the MS/MS Ion Search page on the local masco website. The protein identification results were obtained based on the primary mass spectrometry of the peptide segments resulting from enzyme digestion. Parameter: Trypsin digestion was detected and two missed cleavage sites were set as a fixed modification. The alkylation of cysteine was set as a fixed modification. The oxidation of methionine was set as a variable modification. The database used for identification was NCBprot.

TABLE 2

Molecular weight detected by mass spectrometry and corresponding peptides for C7P7

GFPGVPGGTGPKGDR (SEQ ID NO: 11)

GFPGVPGGTGPKGDRGETGSK (SEQ ID NO: 12)

GLRGEPGFPGVPGGTGPK (SEQ ID NO: 13)

GLRGEPGFPGVPGGTGPKGDR (SEQ ID NO: 14)

GEPGFPGVPGGTGPK (SEQ ID NO: 15)

GEPGFPGVPGGTGPKGDR (SEQ ID NO: 16)

GEPGFPGVPGGTGPKGDRGETGSK (SEQ ID NO: 17)

GDRGETGSKGEQGLPGER (SEQ ID NO: 18)

GETGSKGEQGLPGER (SEQ ID NO: 19)

GEQGLPGER (SEQ ID NO: 20)

GFPGVPGGTGPKGDRGETGSKGEQGLPGERGLRGEPGFPGVPGGTGPKGD
RGETGSKGEQGLPGERGLRGEPGFPGVPGGTGPKGDRGETGSKGEQGLPG
ERGLRGEPGFPGVPGGTGPKGDRGETGSKGEQGLPGERGLRGEPGFPGVP
GGTGPKGDRGETGSKGEQGLPGERGLRGEPGFPGVPGGTGPKGDRGETGS
KGEQGLPGERGLRGEPGFPGVPGGTGPKGDRGETGSKGEQGLPGERGLRG
EPGFPGVPGGTGPKGDRGETGSKGEQGLPGERGLRGEP (SEQ ID NO:
21)

The coverage rate of the detected polypeptide segments was 97.91% compared with the theoretical sequence, thus the detection results were very credible.

TABLE 3

Molecular weight detected by mass spectrometry and corresponding peptides for C7P11

| Observed value | Mr (predicted value) | Peptide |
| --- | --- | --- |
| 3883.1911 | 3882.1838 | GLTGPTGAVGLPGPPGPSGLVGPQGSPGLPG QVGETGKPGAPGR (SEQ ID NO: 22) |
| 2515.2506 | 2514.2434 | DGASGKDGDRGSPGVPGSPGLPGPVGPK (SEQ ID NO: 23) |
| 2000.0284 | 1999.0211 | DGDRGSPGVPCSPGLPGPVGPK (SEQ ID NO: 24) |
| 2763.3720 | 2762.3647 | DGDRGSPGVPCSPGLPGPVGPKGEPGPTGAP (SEQ ID NO: 25) |
| 1556.8616 | 1555.8543 | GSPGVPGSPGLPGPVGPK(SEQ ID NO: 26) |
| 2320.1634 | 2319.1562 | GSPGVPGSPGLPGPVGPKGEPGPTGAP (SEQ ID NO: 27) |

GLTGPTGAVGLPGPPGPSGLVGPQGSPGLPGQVGETGKPGAPGRDGASGK
DGDRGSPGVPGSPGLPGPVGPKGEPGPTGAPGLTGPTGAVGLPGPPGPSG
LVGPQGSPGLPGQVGETGKPGAPGRDGASGKDGDRGSPGVPGSPGLPGPV
GPKGEPGPTGAPGLTGPTGAVGLPGPPGPSGLVGPQGSPGLPGQVGETGK
PGAPGRDGASGKDGDRGSPGVPGSPGLPGPVGPKGEPGPTGAPGLTGPTG
AVGLPGPPGPSGLVGPQGSPGLPGQVGETGKPGAPGRDGASGKDGDRGSP
GVPGSPGLPGPVGPKGEPGPTGAP (SEQ ID NO: 28)

The coverage rate of the detected polypeptide segments was 100% compared with the theoretical sequence, thus the detection results were very credible.

TABLE 4

Molecular weight detected by mass spectrometry
and corresponding peptides for C7P13

GFKGDPGEPGAKGDR (SEQ ID NO: 30)

GDPGEPGAKGDR (SEQ ID NO: 31)

GDRGLPGPR (SEQ ID NO: 32)

AGEPGDPGEDGQK (SEQ ID NO: 33)

AGEPGDPGEDGQKGAPGPK (SEQ ID NO: 34)

GEPGAKGDRGLPGPRGEKGEAGRAGEPGDPGEDGQKGAPGPKGFKGDPGE
PGAKGDRGLPGPRGEKGEAGRAGEPGDPGEDGQKGAPGPKGFKGDPGEPG
AKGDRGLPGPRGEKGEAGRAGEPGDPGEDGQKGAPGPKGFKGDPGEPGAK

TABLE 4-continued

Molecular weight detected by mass spectrometry
and corresponding peptides for C7P13

GDRGLPGPRGEKGEAGRAGEPGDPGEDGQKGAPGPKGFKGDPGEPGAKGD
RGLPGPRGEKGEAGRAGEPGDPGEDGQKGAPGPKGFKGDPGEKGEAGRAG
EPGDPGEDGQKGAPGPKGFKGDP (SEQ ID NO: 35)

The coverage rate of the detected polypeptide segments was 93.75% compared with the theoretical sequence, thus the detection results were very credible.

The above examples are preferred embodiments of the present application, but the embodiments of the present application are not limited by the above examples. Any other changes, modifications, substitutions, combinations, or simplifications without departing from the spirit and principles of the present application shall be equivalent replacements and shall be encompassed in the scope of protection of the present application.

The invention claimed is:

1. A polypeptide which consists of an amino acid sequence of (repeating unit)$_n$ or is 90%-99% identical to the amino acid sequence of (repeating unit)», wherein the repeating unit consists of the amino acid sequence of SEQ ID NO: 1, wherein each repeating unit is directly linked, wherein the number n of the repeating unit is 6-10, and wherein the polypeptide has the ability to promote cell proliferation.

2. The polypeptide according to claim 1, wherein the polypeptide consists of the amino acid sequence of SEQ ID NO: 4 or is 90%-99% identity to the amino acid sequence of SEQ ID NO: 4.

3. The polypeptide according to claim 1, wherein the polypeptide is a recombinant, and wherein the amino acid sequence of the repeating unit is derived from human type VII collagen.

4. A compositions comprising the polypeptide according to claim 1.

5. The composition according to claim 4, wherein the composition is one or more of biological dressings, human body biomimetic materials, materials for plastic surgery and aesthetics, organoid culture materials, cardiovascular stent materials, coating materials, tissue injection and filling materials, ophthalmic materials, gynaecology and obstetrics biological materials, nerve repair and regeneration materials, liver tissue materials, vascular repair and regeneration materials, artificial organ biomaterials, cosmetic raw materials, medicinal auxiliary materials and food additives.

6. A method for producing the polypeptide according to claim 1, comprising:

(1) cultivating host cells comprising a nucleic acid encoding the polypeptide under an appropriate culture condition;

(2) harvesting the host cells and/or a culture medium comprising the polypeptide; and (3) purifying the polypeptide.

7. A method for promoting the proliferation of a cell, comprising contacting the cell with the polypeptide according to claim 1.

8. The method according to claim 7, wherein the cell is an animal cell.

\* \* \* \* \*

SEQUENCE LISTING

```
Sequence total quantity: 35
SEQ ID NO: 1              moltype = AA  length = 36
FEATURE                   Location/Qualifiers
source                    1..36
                          mol_type = protein
                          organism = Homo sapiens
SEQUENCE: 1
GFPGVPGGTG PKGDRGETGS KGEQGLPGER GLRGEP                      36

SEQ ID NO: 2              moltype = AA  length = 81
FEATURE                   Location/Qualifiers
source                    1..81
                          mol_type = protein
                          organism = Homo sapiens
SEQUENCE: 2
GLTGPTGAVG LPGPPGPSGL VGPQGSPGLP GQVGETGKPG APGRDGASGK DGDRGSPGVP   60
GSPGLPGPVG PKGEPGPTGA P                                       81

SEQ ID NO: 3              moltype = AA  length = 48
FEATURE                   Location/Qualifiers
source                    1..48
                          mol_type = protein
                          organism = Homo sapiens
SEQUENCE: 3
GEPGAKGDRG LPGPRGEKGE AGRAGEPGDP GEDGQKGAPG PKGFKGDP            48

SEQ ID NO: 4              moltype = AA  length = 288
FEATURE                   Location/Qualifiers
source                    1..288
                          mol_type = protein
                          organism = synthetic construct
SEQUENCE: 4
GFPGVPGGTG PKGDRGETGS KGEQGLPGER GLRGEPGFPG VPGGTGPKGD RGETGSKGEQ   60
GLPGERGLRG EPGFPGVPGG TGPKGDRGET GSKGEQGLPG ERGLRGEPGF PGVPGGTGPK  120
GDRGETGSKG EQGLPGERGL RGEPGFPGVP GGTGPKGDRG ETGSKGEQGL PGERGLRGEP  180
GFPGVPGGTG PKGDRGETGS KGEQGLPGER GLRGEPGFPG VPGGTGPKGD RGETGSKGEQ  240
GLPGERGLRG EPGFPGVPGG TGPKGDRGET GSKGEQGLPG ERGLRGEP            288

SEQ ID NO: 5              moltype = AA  length = 324
FEATURE                   Location/Qualifiers
source                    1..324
                          mol_type = protein
                          organism = synthetic construct
SEQUENCE: 5
GLTGPTGAVG LPGPPGPSGL VGPQGSPGLP GQVGETGKPG APGRDGASGK DGDRGSPGVP   60
GSPGLPGPVG PKGEPGPTGA PGLTGPTGAV GLPGPPGPSG LVGPQGSPGL PGQVGETGKP  120
GAPGRDGASG KDGDRGSPGV PGSPGLPGPV GPKGEPGPTG APGLTGPTGA VGLPGPPGPS  180
GLVGPQGSPG LPGQVGETGK PGAPGRDGAS GKDGDRGSPG VPGSPGLPGP VGPKGEPGPT  240
GAPGLTGPTG AVGLPGPPGP SGLVGPQGSP GLPGQVGETG KPGAPGRDGA SGKDGDRGSP  300
GVPGSPGLPG PVGPKGEPGP TGAP                                    324

SEQ ID NO: 6              moltype = AA  length = 288
FEATURE                   Location/Qualifiers
source                    1..288
```

```
                                mol_type = protein
                                organism = synthetic construct
SEQUENCE: 6
GEPGAKGDRG LPGPRGEKGE AGRAGEPGDP GEDGQKGAPG PKGFKGDPGE PGAKGDRGLP   60
GPRGEKGEAG RAGEPGDPGE DGQKGAPGPK GFKGDPGEPG AKGDRGLPGP RGEKGEAGRA  120
GEPGDPGEDG QKGAPGPKGF KGDPGEPGAK GDRGLPGPRG EKGEAGRAGE PGDPGEDGQK  180
GAPGPKGFKG DPGEPGAKGD RGLPGPRGEK GEAGRAGEPG DPGEDGQKGA PGPKGFKGDP  240
GEPGAKGDRG LPGPRGEKGE AGRAGEPGDP GEDGQKGAPG PKGFKGDP                288

SEQ ID NO: 7                moltype = DNA  length = 864
FEATURE                     Location/Qualifiers
source                      1..864
                            mol_type = other DNA
                            organism = synthetic construct
SEQUENCE: 7
ggatttcccg gggtcccggg aggcaccggc cctaaaggcg atcgtggtga aaccggcagc   60
aagggcgagc agggtctgcc gggcgagcgc ggtttgagag cgaaccggg ttttccaggc  120
gtgccgggcg gtacgggtcc gaagggtgac cgtggcgaaa ccggcagcaa gggtgaacaa  180
ggtttaccgg gtgaacgcgg tctgcgtggt gagccgggct tcccaggtgt tccgggcgga  240
accggtccta aaggtgatcg tggcgaaacc ggttccaaag cgaacaagg tcttccgggt  300
gagcgcggtc tgcgtggcga accgggtttc ccgggcgtgc cgggaggcac cggcccaaag  360
ggcgaccgcg gagaaaccgg cagcaaaggc gagcagggcc tgccgggtga acgtggcctg  420
cgtggtgagc cgggattccc gggtgttccg ggcggcaccg gtccgaaagg tgatcgtggt  480
gaaaccggta gcaagggtga acagggtctg ccgggcgagc gcggcttgag aggtgagcct  540
ggtttttccgg gggtgcccgg cggtacgggc ccgaaaggcg accgtggcga aaccggttct  600
aagggtgagc agggtctgcc gggtgagcgt ggtctgcgcg gtgagccggg tttcccgggc  660
gttccgggtg gcactggtcc gaagggcgac cgtggcgaga ctggctcgaa aggtgaacag  720
ggttttgccgg gtgagcgtgg tctgcgtggt gagccgggtt ttccgggcgt gccgggtggc  780
acgggcccaa aaggcgatcg tggtgagacc ggttccaagg cgagcaagg tctgccgggc  840
gagcgcggtc tccgcggtga accg                                         864

SEQ ID NO: 8                moltype = DNA  length = 972
FEATURE                     Location/Qualifiers
source                      1..972
                            mol_type = other DNA
                            organism = synthetic construct
SEQUENCE: 8
ggactaacag ggccgaccgg tgcggtcggc ctgccgggac caccgggccc cagcggtctg   60
gttggtcctc agggttcccc gggtcttccg ggcaggttg gtgagacagg caagccggt  120
gcgccgggcc gtgacggtgc ctctggtaaa gacggcgatc gtggttcgcc gggcgttccg  180
ggttcgccgg gtctgccggg tccggtcggt ccgaaaggtg aaccggggcc cactggtgcg  240
ccaggcttga ccggtccgac cggtgcggtt ggcctcccgg cccaccggg accgagcggt  300
ctggttggcc cacaaggttc cccgggctta ccgggccagg ttggagaaac cggtaagccg  360
ggtgcaccgg ggcgcgacgg cgcaagcggt aaggacggcg accgcggtag cccgggcgtg  420
ccgggtagcc cgggcctgcc gggcccggtg ggccccaagg gtgagccggg accgaccggc  480
gctccggggt tgaccggtcc aacgggcgct gtgggcctgc cgggtccacc gggtccgagc  540
ggtctggttg gcccgcaggg tagcccgggt ctgccgggcc aagttggtga aaccggtaaa  600
ccgggagcac caggccgtga tggtgcctcc ggtaaggacg gcgatcgcgg ttctccgggc  660
gtcccgggct cccccgggtct gccgggcccg gtgggtccga aagtgagcc gggccccgacg  720
ggcgcgccgg gcttgaccgg cccgacgggt gctgtgggtc tgccgggccc tccgggtcca  780
agcggtctgt tgggccctca aggttctccg ggtctgccgg gacaggtggg cgaaaccggt  840
aagccgggtg cgccaggtcg tgatggcgcg agcggcaaag atggtgatcg tggcagtccg  900
ggggtgccgg gcagcccggg cttgccgggt ccagtaggtc cgaaaggcga gccgggccg  960
accggcgcgc ct                                                      972

SEQ ID NO: 9                moltype = DNA  length = 864
FEATURE                     Location/Qualifiers
source                      1..864
                            mol_type = other DNA
                            organism = synthetic construct
SEQUENCE: 9
ggagaacccg gggcgaaggg cgaccgcggt ctgccgggtc cgcgtggtga aaaaggtgag   60
gcgggccgcg caggcgaacc gggtgacccg ggcgaggatg gtcagaaagg cgcgccaggt  120
ccgaaaggtt ttaaaggcga tccgggcgaa ccgggtgcca gggtctgcca aggtctgccg  180
ggtccgcgtg gcgaaaaggg tgaagcgggt cgtgcgggtg aaccgggtga cccgggcgag  240
gacggtcaga agggcgcgcc aggtccgaaa ggcttcaaag gtgacccggg tgaaccgggc  300
gcgaaaggca ccgtggtttt accgggtccg cgtggtgaga aggggggaggc tggtcgtgcc  360
ggtgaaccgg gcgacccagg cgaggatggt cagaaaggcg cgcctggtcc caagggcttc  420
aagggcgacc cgggtgaacc gggtgccaaa gggatccggg gtttgccagg tcctcgcggt  480
gaaaagggcc aggctggtcg cgctggtgag ccgggcgacc cgggtgaaga tggtcaaaaa  540
ggcgctccgg gtccgaaggg ttttaaaggt gatccgggcg agccgggtgc gaagggcgat  600
cgtggcctgc cgggcccacg tggtgagaaa ggcgaggccg gtcgtgcagg cgaaccgggt  660
gaccccggcg aagatggcca aaaggggtgcg cctggcccga agggattcaa aggcgatccg  720
ggtgagccgg gcgcgaaagg cgaccgcggc ctgccgggtc cgcgtggtga aagggggcgag  780
gcaggccgtg caggtgaacc ggtgacccg ggtgaggatg gtcaaaaagg tgctccgggt  840
ccgaagggct ttaagggcga cccg                                         864

SEQ ID NO: 10               moltype = AA  length = 12
FEATURE                     Location/Qualifiers
```

-continued

```
source                      1..12
                            mol_type = protein
                            organism = synthetic construct
SEQUENCE: 10
GFPGVPGGTG PK                                                                    12

SEQ ID NO: 11               moltype = AA   length = 15
FEATURE                     Location/Qualifiers
source                      1..15
                            mol_type = protein
                            organism = synthetic construct
SEQUENCE: 11
GFPGVPGGTG PKGDR                                                                 15

SEQ ID NO: 12               moltype = AA   length = 21
FEATURE                     Location/Qualifiers
source                      1..21
                            mol_type = protein
                            organism = synthetic construct
SEQUENCE: 12
GFPGVPGGTG PKGDRGETGS K                                                          21

SEQ ID NO: 13               moltype = AA   length = 18
FEATURE                     Location/Qualifiers
source                      1..18
                            mol_type = protein
                            organism = synthetic construct
SEQUENCE: 13
GLRGEPGFPG VPGGTGPK                                                              18

SEQ ID NO: 14               moltype = AA   length = 21
FEATURE                     Location/Qualifiers
source                      1..21
                            mol_type = protein
                            organism = synthetic construct
SEQUENCE: 14
GLRGEPGFPG VPGGTGPKGD R                                                          21

SEQ ID NO: 15               moltype = AA   length = 15
FEATURE                     Location/Qualifiers
source                      1..15
                            mol_type = protein
                            organism = synthetic construct
SEQUENCE: 15
GEPGFPGVPG GTGPK                                                                 15

SEQ ID NO: 16               moltype = AA   length = 18
FEATURE                     Location/Qualifiers
source                      1..18
                            mol_type = protein
                            organism = synthetic construct
SEQUENCE: 16
GEPGFPGVPG GTGPKGDR                                                              18

SEQ ID NO: 17               moltype = AA   length = 24
FEATURE                     Location/Qualifiers
source                      1..24
                            mol_type = protein
                            organism = synthetic construct
SEQUENCE: 17
GEPGFPGVPG GTGPKGDRGE TGSK                                                       24

SEQ ID NO: 18               moltype = AA   length = 18
FEATURE                     Location/Qualifiers
source                      1..18
                            mol_type = protein
                            organism = synthetic construct
SEQUENCE: 18
GDRGETGSKG EQGLPGER                                                              18

SEQ ID NO: 19               moltype = AA   length = 15
FEATURE                     Location/Qualifiers
source                      1..15
                            mol_type = protein
                            organism = synthetic construct
SEQUENCE: 19
GETGSKGEQG LPGER                                                                 15

SEQ ID NO: 20               moltype = AA   length = 9
```

-continued

```
FEATURE              Location/Qualifiers
source               1..9
                     mol_type = protein
                     organism = synthetic construct
SEQUENCE: 20
GEQGLPGER                                                            9

SEQ ID NO: 21        moltype = AA  length = 288
FEATURE              Location/Qualifiers
source               1..288
                     mol_type = protein
                     organism = synthetic construct
SEQUENCE: 21
GFPGVPGGTG PKGDRGETGS KGEQGLPGER GLRGEPGFPG VPGGTGPKGD RGETGSKGEQ   60
GLPGERGLRG EPGFPGVPGG TGPKGDRGET GSKGEQGLPG ERGLRGEPGF PGVPGGTGPK   120
GDRGETGSKG EQGLPGERGL RGEPGFPGVP GGTGPKGDRG ETGSKGEQGL PGERGLRGEP   180
GFPGVPGGTG PKGDRGETGS KGEQGLPGER GLRGEPGFPG VPGGTGPKGD RGETGSKGEQ   240
GLPGERGLRG EPGFPGVPGG TGPKGDRGET GSKGEQGLPG ERGLRGEP                288

SEQ ID NO: 22        moltype = AA  length = 44
FEATURE              Location/Qualifiers
source               1..44
                     mol_type = protein
                     organism = synthetic construct
SEQUENCE: 22
GLTGPTGAVG LPGPPGPSGL VGPQGSPGLP GQVGETGKPG APGR                    44

SEQ ID NO: 23        moltype = AA  length = 28
FEATURE              Location/Qualifiers
source               1..28
                     mol_type = protein
                     organism = synthetic construct
SEQUENCE: 23
DGASGKDGDR GSPGVPGSPG LPGPVGPK                                       28

SEQ ID NO: 24        moltype = AA  length = 22
FEATURE              Location/Qualifiers
source               1..22
                     mol_type = protein
                     organism = synthetic construct
SEQUENCE: 24
DGDRGSPGVP CSPGLPGPVG PK                                             22

SEQ ID NO: 25        moltype = AA  length = 31
FEATURE              Location/Qualifiers
source               1..31
                     mol_type = protein
                     organism = synthetic construct
SEQUENCE: 25
DGDRGSPGVP CSPGLPGPVG PKGEPGPTGA P                                   31

SEQ ID NO: 26        moltype = AA  length = 18
FEATURE              Location/Qualifiers
source               1..18
                     mol_type = protein
                     organism = synthetic construct
SEQUENCE: 26
GSPGVPGSPG LPGPVGPK                                                  18

SEQ ID NO: 27        moltype = AA  length = 27
FEATURE              Location/Qualifiers
source               1..27
                     mol_type = protein
                     organism = synthetic construct
SEQUENCE: 27
GSPGVPGSPG LPGPVGPKGE PGPTGAP                                        27

SEQ ID NO: 28        moltype = AA  length = 324
FEATURE              Location/Qualifiers
source               1..324
                     mol_type = protein
                     organism = synthetic construct
SEQUENCE: 28
GLTGPTGAVG LPGPPGPSGL VGPQGSPGLP GQVGETGKPG APGRDGASGK DGDRGSPGVP   60
GSPGLPGPVG PKGEPGPTGA PGLTGPTGAV GLPGPPGPSG LVGPQGSPGL PGQVGETGKP   120
GAPGRDGASG KDGDRGSPGV PGSPGLPGP GPKGEPGPTG APGLTGPTGA VGLPGPPGPS    180
GLVGPQGSPG LPGQVGETGK PGAPGRDGAS GKDGDRGSPG VPGSPGLPGP VGPKGEPGPT   240
GAPGLTGPTG AVGLPGPPGP SGLVGPQGSP GLPGQVGETG KPGAPGRDGA SGKDGDRGSP   300
GVPGSPGLPG PVGPKGEPGP TGAP                                          324
```

-continued

```
SEQ ID NO: 29            moltype = AA  length = 12
FEATURE                  Location/Qualifiers
source                   1..12
                         mol_type = protein
                         organism = synthetic construct
SEQUENCE: 29
GFKGDPGEPG AK                                                   12

SEQ ID NO: 30            moltype = AA  length = 15
FEATURE                  Location/Qualifiers
source                   1..15
                         mol_type = protein
                         organism = synthetic construct
SEQUENCE: 30
GFKGDPGEPG AKGDR                                               15

SEQ ID NO: 31            moltype = AA  length = 12
FEATURE                  Location/Qualifiers
source                   1..12
                         mol_type = protein
                         organism = synthetic construct
SEQUENCE: 31
GDPGEPGAKG DR                                                  12

SEQ ID NO: 32            moltype = AA  length = 9
FEATURE                  Location/Qualifiers
source                   1..9
                         mol_type = protein
                         organism = synthetic construct
SEQUENCE: 32
GDRGLPGPR                                                      9

SEQ ID NO: 33            moltype = AA  length = 13
FEATURE                  Location/Qualifiers
source                   1..13
                         mol_type = protein
                         organism = synthetic construct
SEQUENCE: 33
AGEPGDPGED GQK                                                 13

SEQ ID NO: 34            moltype = AA  length = 19
FEATURE                  Location/Qualifiers
source                   1..19
                         mol_type = protein
                         organism = synthetic construct
SEQUENCE: 34
AGEPGDPGED GQKGAPGPK                                           19

SEQ ID NO: 35            moltype = AA  length = 273
FEATURE                  Location/Qualifiers
source                   1..273
                         mol_type = protein
                         organism = synthetic construct
SEQUENCE: 35
GEPGAKGDRG LPGPRGEKGE AGRAGEPGDP GEDGQKGAPG PKGFKGDPGE PGAKGDRGLP  60
GPRGEKGEAG RAGEPGDPGE DGQKGAPGPK GFKGDPGEPG AKGDRGLPGP RGEKGEAGRA  120
GEPGDPGEDG QKGAPGPKGF KGDPGEPGAK GDRGLPGPRG EKGEAGRAGE PGDPGEDGQK  180
GAPGPKGFKG DPGEPGAKGD RGLPGPRGEK GEAGRAGEPG DPGEDGQKGA PGPKGFKGDP  240
GEKGEAGRAG EPGDPGEDGQ KGAPGPKGFK GDP                             273
```